US006667026B1

(12) United States Patent
Goldman et al.

(10) Patent No.: US 6,667,026 B1
(45) Date of Patent: Dec. 23, 2003

(54) ALLERGIC CONTACT DERMATITIS TREATMENT AND COMPOSITION THEREFOR

(75) Inventors: Gavriel Goldman, Dingmans Ferry, PA (US); Mitchell Lapidus, Whippany, NJ (US)

(73) Assignee: Pocono Falls, Inc., Whippany, NJ (US)

( * ) Notice: Subject to any disclaimer, the term of this patent is extended or adjusted under 35 U.S.C. 154(b) by 27 days.

(21) Appl. No.: 10/100,476

(22) Filed: Mar. 15, 2002

(51) Int. Cl.⁷ .................. A61K 35/78; A61K 39/385; A61K 31/56; A61K 31/045; A61K 31/05

(52) U.S. Cl. .................. 424/47; 424/725; 424/771; 424/776; 514/178; 514/724; 514/731; 514/862

(58) Field of Search .................. 427/47, 725, 771; 427/776; 514/862, 178, 724, 731

(56) References Cited

U.S. PATENT DOCUMENTS

| | | | |
|---|---|---|---|
| 5,080,900 A | 1/1992 | Stanley | 424/195.1 |
| 5,443,847 A | 8/1995 | West | 424/639 |
| 6,113,929 A | 9/2000 | Karl | 424/401 |
| 6,149,947 A | 11/2000 | Hon et al. | 424/641 |
| 2003/0082244 A1 * | 5/2003 | Yoshida et al. | 424/725 |

OTHER PUBLICATIONS

Hodge and Osman, *Organic Chemistry*, Maillard Reactions article, pp. 82–87.
Federal Register, *Skin Protectant Drug Products* . . . , 21CRF Part 347, vol. 54, No. 190 issued Oct. 3, 1989; pp. 40808–40827.

* cited by examiner

*Primary Examiner*—Michael G. Hartley
*Assistant Examiner*—Marina Lamm
(74) *Attorney, Agent, or Firm*—Siegmar Silber, Esq.

(57) ABSTRACT

A topical composition is disclosed for reducing a urushiol-induced allergic response and the dermatitis associated therewith. The composition is a preparation having an acorn derivative and a nontoxic dermatologically acceptable aqueous dispersion material. The acorn derivative is acorn ash, acorn mash, roasted acorn, or acorn extract and comprises about 0.1 to 50 percent by weight of the treating preparation. After the initial preparation, preservatives are then added. Optionally, additional ingredients such as surfactants and emulsifying agents, antihistamines, topical anesthetics, colloidal oatmeal, topical antipruritics, astringents, and emollients may be added to the aqueous acorn dispersion. With processing varied according the examples provided, the ingredients are combined so as to create sprays, creams, gels, ointments, and lotions.

10 Claims, No Drawings

ALLERGIC CONTACT DERMATITIS TREATMENT AND COMPOSITION THEREFOR

BACKGROUND OF THE INVENTION

1. Field of the Invention

This invention relates to a treatment for allergic contact dermatitis. More particularly, the invention relates to a dermatitis treatment with a topical composition having an active ingredient of an acorn derivative, namely, a powdered acorn or an acorn extract from acorn ash, acorn mash, or roasted acorn.

2. Background Information

Poison ivy, poison oak, or poison sumac dermatitis is often referred to as rhus dermatitis and is a common, seasonal, allergic contact dermatitis. In the United States, poison ivy (*Toxicodendron radicans*) and poison oak (*Toxicodendron diversilobum* or *quercifolium*) are the main causes of rhus dermatitis. Poison ivy, which is particularly abundant in eastern United States and southeastern Canada, is found as either a shrub or a vine.

Before contact dermatitis develops, sensitization is experienced whereby, upon exposure to the toxic agent, toxicodendrol, the individual acquires hypersensitivity thereto. Therefore, not everyone who is exposed to the plants has an allergic reaction. However, it is estimated that at least 70% of the U.S. population could react after casual exposure to the plants.

Toxicodendrol, the previously mentioned toxic agent, is a phenolic oleoresin that is present in all the poisonous species. Toxicodendrol contains the complex active principle urushiol, which, in turn, is distributed widely in the roots, stems, leaves, and fruit of the plant, but not in the flower, pollen, or plant epidermis. Therefore, contact with the intact epidermis of the plant is harmless and contact dermatitis occurs only upon contact with a bruised or injured plant or with a carrier of the juices therefrom, e.g. from the coat of a dog. As little as 1 µg of crude urushiol causes dermatitis in sensitive individuals.

The natural course of contact dermatitis is divided into two phases; a sensitization phase, during which a specific hypersensitivity to the allergen is acquired, supra, and an elicitation phase, during which subsequent contact with the allergen elicits a visible dermatologic response. The reaction time—the interval between contact with the allergen and the appearance of the response—varies with the degree of sensitivity and the amount of allergen contacted. Reaction time is usually between 12 hours and up to 2 to 3 days. This interval is a result of delayed hypersensitivity reactions involving cell-mediated immunity.

In the elicitation phase, following exposure to the antigen, there develops an initial reaction, namely, an erythema or rash. This is followed by the development of raised lesions (erythematous macules and papules). Finally, fluid accumulation causes the formation of vesicles and bullae in the epidermis.

In preparing for this application several references became known to the inventors hereof. Both chemical and medical databases revealed sparse information on the principal active ingredient hereof, namely, acorn derivatives; however, the U.S. Department of Agriculture (USDA) and the International Food Ingredient Council Foundation (IFIC) have ascertained basic nutritional information for the acorn. According to the analysis provided, the acorn, like other nuts, is composed or water, protein, lipid, carbohydrate, minerals, and vitamins. For a more detailed account as to content of this ingredient, see infra.

Further and also in preparing for this application several patents became known to the inventors hereof in which oak bark ash is described as a therapeutic agent in treating poison ivy symptoms. R. Thomas Stanley in U.S. Pat. No. 5,080,900 describes the use of oak bark ash and later technical developments are described by David N. Hon and R. Thomas Stanley in U.S. Pat. No. 6,149,947. Although reported as having therapeutic advantages, Karl in U.S. Pat. No. 6,113,929 indicates that the tannic acid in the oak bark ash formulations acts as an astringent and does not remove all the oleoresin, toxicodendrol, from the skin, However, when used after an alkaline cleanser, removes some of the resin, the oak bark preparation removes the remaining resin portion and closes the skin pores to prevent residual resin working its way into the pores. There is thus some question as to the efficacy of astringent preparations, particularly oak bark ash, and the methodology with which the same should be used.

By way of further background as to the active ingredient, the acorn derivative, the heating of acorns generate, as would be expected, Maillard reaction products. Initial reactions of Maillard reaction involves condensation, enolization, and Amadori rearrangement of proteins, sugars, and free amino groups. Intermediate reactions involve sugar dehydration, sugar fragmentation, formations of dicarbonyl compounds, reductones, and pigments. During the final stages of Maillard reactions, red-brown and dark brown color is generated. The reactions involved in the final stages of Maillard reaction involve aldol condensation, polymerization, and Strecker degradation. Roasted aromas develop as well as colloidal and insoluble melanoidins also form. The acorn derivatives herein, including those from roasted acorns, are differentiated from oak bark and tannic-acid-containing products by the constituents mentioned and by a pH above 4.5. are above what would be expected for a high tannic acid material. It is believed that trace amounts of tannins occur in acorn derivatives and are believed to stem from the shells and hats of the acorn.

West U.S. Pat. No. 5,443,847 identified a detoxification agent for urushiol using divalent metals such as manganese. West '847 indicates that organic molecules containing hydroxyl (—OH) and carboxyl (—COOH) groups are reactive to polyvalent metals and that urushiol has two hydroxyl groups that can form stable chelates by replacing the hydrogens with divalent metals that are present in the agent. West claims the use and method of manganese salts (0.01 to 10.0 percent Mn) in an aqueous solution between pH 5 and 7.

The discussion of the above documents is not intended as an admission that any such document constitutes prior art against the claims of the present application. Applicant does not waive any right to take any action that would be appropriate to antedate or otherwise remove any listed document as a competent reference against the claims of the present application.

SUMMARY AND DESCRIPTION OF THE PREFERRED EMBODIMENT

Introduction

In general terms, the invention disclosed hereby includes an aqueous solution of an acorn derivative suitable for application to the site of contact dermatitis. The acorn derivatives as discussed hereinbelow are extracts, suspensions, and dispersions prepared from acorn ash, acorn mash, and roasted acorns. Acorns utilized in the present invention are from Red Oak (*Quercus rupra*), Black Oak (*Quercus shumardi* i Buckl.) Scarlet Oak (*Quercus coccinea* Muenchb.), Willow Oak (*Quercus phellos* L.) and other species of the Erythrobalanus group.

In the description which follows the term treating preparations is defined as solutions, suspensions, or emulsions in the form of topical ointments, creams, lotions and sprays. In the formulations of the present invention varying amounts of acorn derivatives have been found to be efficacious in treating the allergic response induced by the urushiol resin and the dermatitis arising therefrom. Thus, treating preparations having from 0.1 to 50 percent by weight of acorn derivative are set forth. The treating preparations, namely solutions, suspensions, and emulsions hereof have, in addition to the acorn derivative, a nontoxic dermatologically acceptable aqueous dispersion material.

Various topical compositions forming sprays, creams and ointments require in addition to the acorn derivative and water such inactive components as surfactants, antioxidants, emulsifiers, stabilizers, dispersants, and preservatives. In another aspect of the invention additional active components of the topical composition are disclosed such as anesthetics, antipruritics and antihistamines.

The Prophylactic Effect and the Mechanism of Action of the Acorn Extract

As discussed in some detail in the Background Information, it is believed that the allergic response to urushiol has an initial sensitization phase followed by a delayed hypersensitivity reaction in the dermal layers of the skin. While the exact reaction mechanism is not fully understood, researchers believe that the urushiol resins enter the superficial layers of the human dermis where it attaches to tissue proteins to produce a hapten in about 10 minutes or less. The protein molecules are attached on the surface of specialized white blood cells known as Langerhans cells in the epidermis and to macrophages in the dermis skin layers. The Langerhans cells communicate the antigen information to inducer lymphocyte cells, which proliferate into circulating T-memory and T-effector lymphocytes. The immune lymphocytes are now sensitized to additional urushiol entry into the skin layers.

With subsequent urushiol exposure, the subject has a delayed hypersensitivity reaction, which allows T-cells to invade the skin area containing the newly deposited urushiol. It is further hypothesized that the acorn extract provides a physical and mechanical barrier which protects exposed skin or mucous membrane surfaces from harmful stimuli and annoying irritants. Exposed skin or mucous membranes surfaces are isolated from harmful stimuli and annoying irritants because the physical and chemical properties of acorn derivatives include a protective demulcent effect. It is also hypothesized that the proteins, carbohydrates, lipids, divalent metals in the acorn derivatives, and the Maillard reaction components in the acorn extract preferentially bind and thereby inactivate urushiol resin.

Additionally, the acorn extract also binds and inactivates the urushiol components during the elicitation phase of the antigenic response. The aqueous acorn extract hereof also controls the osmotic pressure of water with respect to the skin and permits adequate water to enter into the stratum corneum. The acorn extract leaves a thin occlusive film or coating on the skin which retains the absorbed moisture. As a result of this coating, a dual action occurs, namely: (1) the acorn extract proteins, carbohydrate, divalent metals and Maillard reaction products bind the urushiol stimuli components and reduce further antigenic response; and, (2) the lipid, protein, carbohydrate, and Maillard reaction components protect against urushiol irritation by moisturizing the skin. Acorn extract thereby acts as an antipuritic and has a generally soothing demulcent effect.

Acorn Derivatives

Several examples of various ointments, creams, aqueous solutions, sprays and the like for the treatment of contact dermatitis are presented hereinbelow. All of the preparations contain a most efficacious active ingredient, namely, a vegetable product derived from the acorn. The acorns utilized can be from Red Oak (*Quercus rupra*), Black Oak (*Quercus shumardi* i Buckl.) Scarlet Oak (*Quercus coccinea* Muenchb.), Willow Oak (*Quercus phellos* L.) and other species of the Erythrobalanus group. For purposes of this application an acorn derivative is defined as any of the following forms; an acorn powder produced by roasting the acorn nuts, shells and caps and further processing the product thereof by, for example, triturating, grinding, milling, and/or screening; an acorn ash or the solid residue remaining after burning the combustible portion; an acorn mash, namely, a solution of crushed acorn nuts; and, an acorn extract, namely, a suspension or dispersion using powder, ash, and/or mash and suitable aqueous and non-aqueous diluents.

Acorn is composed of water, proteins, lipids, carbohydrates, minerals, and vitamins. When the acorn is roasted, the roasting process generates Maillard or sugar-amine reactions and produces sugar fragmentation and other reaction products. In this regard the acorn extract is distinguished from oak bark and tannic acid mentioned, supra, based on composition and Maillard reaction products. While some tannins may be derived from the acorn shells and hats, the coloration of the roasted product suggests the formation of some melanoids as a result of the roasting process.

In one method, prior to preparing an extract, the raw or roasted acorns are converted into ash by burning off the organic materials. The ash inorganic material is cooled and screened to provide a powder.

Preparing the Acorn Extracts

Acorn extract, suspensions, and dispersions for use in the present invention are prepared from raw acorn mash, roasted acorns or acorn ash. Acorn mash is prepared by breaking up the shells and hats of raw acorns in order to expose the inner nut portion of the acorn. Roasted acorns are prepared by heating raw acorns between about 90° C. and about 350° C. for between about 5 minutes to 10 hours. The preferred roasting conditions are 200° C. for one hour. The roasted acorns are cooled then prepared for extraction by breaking up the shells and hats in order to expose the inner portion of the acorn.

Various extracts, suspensions, and dispersions can be prepared by those familiar with the art. The extracts can be prepared from water, super critical $CO_2$, or various polarity solvents. The solvents include alcohols, ethers, hexanes, methylene chloride, and others. The preferred extract, suspension, and dispersion are prepared using water.

The mash or roasted acorns are extracted in water for a period of time. The water temperature can range from about 10° C to 100° C., with stirring for a period of time ranging from 10 minutes to 24 hours in order to prepare an intermediate. The time temperature relationship is also concentration dependent. The preferred extract, suspension, or dispersion is prepared from about 10% material at 100° C. for 1-hour. The intermediate is screened to remove the large particles and thereby reduces the concentration of the acorn extract to about 5%. These extracts may also be filtered. The aqueous extracts in accordance with the invention are complex mixtures of organic and inorganic materials.

The mash or roasted acorns are extracted in intermediate polarity solvents such as alcohol for a period of time. The preferred alcohol is ethanol at room temperature or with slight heating. The alcohol may also be distilled and condensed over the acorn material to provide continuous extraction with pure solvent similar to that used in a soxlet extractor in order to prepare an intermediate. The time temperature relationship is concentration dependent and varies from one concentration to another. The preferred extract from about 10% material at for 1-hour.

The intermediate is screened to remove the large particles and thereby reduces the concentration of the acorn extract to about 5%. These extracts may also be filtered. The alcoholic extracts in accordance with the invention are complex mixtures of organic and inorganic materials. The alcohol may be evaporated off to produce a concentrated extract or used as is to formulate.

The mash or roasted acorns are extracted in non-polar solvents such as hexane, methylene chloride, and ethers for a period of time. The preferred nonpolar solvent is hexane at room temperature or with slight heating. The hexane may also be distilled and condensed over the acorn material to provide continuous extraction with pure solvent similar to that used in a soxlet extractor in order to prepare an intermediate. The time temperature relationship is also concentration dependent. The preferred extract from about 10% material at for 1-hour. The intermediate is screened to remove the large particles and thereby reduces the concentration of the acorn extract to about 5%. These extracts may also be filtered. The nonpolar solvent extracts in accordance with the invention are complex mixtures of organic and inorganic materials. The nonpolar solvent is evaporated off to produce a concentrated extract. Acorn Ash can be used to formulate directly. Additional nonpolar acorn extracts may be prepared by using super critical $CO_2$ extractions techniques. In particular, compositions containing about 0.1% or more, preferably 0.5 to 75% and more preferably 0.5 to 10% or acorn extract according to the invention can be used to treat poison ivy.

Preparing the Compositions

The compositions prepared as described in general hereinbelow are prepared from acorn derivatives, including acorn mash, acorn roast and acorn ash. These ingredients which are initially in particulate form are, prior to manufacturing, screened to select particle size using USA Standard Testing Sieves Nos. 70 to 30, preferably No. 50. Prior to final screening, a particle size reduction step is employed utilizing herringbone-perforated or round-hole-perforated reducing screens. For aqueous dispersions, the screened and reduced particle-size acorn material is then mixed with purified water with a commercially available mixer, such as a Lightnin' Mixer.

After mixing, preservatives are then added to the mixture. If desired additional ingredients such as surfactants and emulsifying agents, antihistamines, topical anesthetics, colloidal oatmeal, topical antipruritics, astringents, and emollients may be added to the aqueous acorn dispersion. The ingredients may be added in such a ratio and processing varied as to create a spray, cream, gel, ointment, or lotion.

The most frequently used preservative for the formulations herein are benzoic acid and derivatives thereof, namely, butylparaben, ethylparaben, methylparaben, propylparaben, sodium benzoate, and mixtures thereof. Typical use of benzoic-acid-derived preservative is a mixture of methylparaben comprising up to 0.3 percent by weight of the treating composition and propylparaben comprising up to 0.1 percent by weight of the treating composition.

Other useful preservatives include alcohol, benzalkonium chloride, benzethonium chloride, benzyl alcohol, bronopol, cetrimide, chlorhexidine, chlorobutanol, chlorocresol, cresol, glycerin, imidurea, phenol, phenoxyethanol, phenylethyl alcohol, phenylmercuric acetate, phenylmercuric borate, phenylmercuric nitrate, potassium sorbate, propylene glycol, sodium propionate, sorbic acid and thimerosal.

Among the inactive ingredients are surfactants and emulsifying agents. These ingredients take on importance as the use thereof improves absorption, coverage, appearance, and feel of the product. Some suitable emulsifying agents are acacia, anionic emulsifying wax, carbomer, carboxymethyl cellulose, cetostearyl alcohol, cetyl alcohol, cholesterol, diethanolamine, glyceryl monostearate, hydrous lanolin, hydroxyethyl cellulose, hydroxypropyl cellulose, hydroxypropyl methylcellulose, lanolin, lanolin alcohols, lecithin, methylcellulose, mineral oil and lanolin alcohols, monobasic sodium phosphate, monoethanolamine, nonionic emulsifying wax, oleic acid, poloxamer, polyoxyethylene alkyl ethers, polyoxyethylene castor oil derivatives, polyoxyethylene sorbitan fatty acid esters, polyoxyethylene stearates, propylene glycol alginate, sodium lauryl sulfate, sorbitan esters, stearic acid, triethanolamine, and xanthan gum. Frequently mixtures of complimentary surfactants are used in a given formulation.

In the examples applying the present invention anionic, cationic and nonionic surfactants are selected. The anionic surfactants are lauryl sulfates, including sodium lauryl sulfate, triethanolamine lauryl sulfate, and ammonium lauryl sulfate; laureth sulfates, including sodium laureth sulfate, triethanolamine laureth sulfate, and ammonium laureth sulfate; sarcosines, including lauryl sarcosine, and sodium lauryl sarcosinate; sulfosuccinates, including disodium oleamine sulfosuccinate, and sodium dioctyl sulfosuccinate; and docusate sodium. The cationic surfactants are benzalkonium chloride, benzethonium chloride, and cetrimide. The nonionic surfactants are glyceryl monooleate, polyvinyl alcohol, sorbitan esters, povidone, crospovidone, polyoxyethylene fatty alcohols, polyoxyethylene sorbitol esters, and alkanolamides. Additionally, in the examples applying the present invention, amphoteric detergents such as betaines, sultaines, and imidazolinium derivatives are used, and particularly ingredients such as cocamidopropyl betaine and sodium lauraminopropionate.

In the ointment and cream preparations hereinbelow, emollients form a vehicle to carry the active ingredients to the site of the urushiol response and the associated dermatitis. The emollient group from which these carriers are selected include allantoin, cetostearyl alcohol, cetyl esters wax, cocoa butter, cholesterol, dimethicone, glycerin, glyceryl monostearate, isopropyl myristate, isopropyl palmitate, kaolin, lecithin, light mineral oil, mineral oil, mineral oil and lanolin alcohols, petrolatum, and petrolatum and lanolin alcohols.

One of the functions of the formulations is to remove the urushiol resin from the skin. This requires astringent activity, and while the acorn derivative provides a satisfactory level of astringency the addition of aluminum acetate, zinc oxide, zinc acetate, sodium bicarbonate, calamine, witch hazel, zinc carbonate, and aluminum hydroxide has been employed to enhance this physical property.

It has been found that the antipruritic activity of the acorn derivative hereof is compatible with other well-known antipruritic agents and when combined therewith provide unexpected synergy. Such agents include phenol, camphor, menthol, hydro-cortisone, hydrocortisone acetate, camphorated metacresol, phenolated sodium, and mixtures thereof. As is shown in the examples which follow the effect is gained by the addition of menthol comprising up to 0.2 percent by weight of the formulation or the addition hydrocortisone acetate comprising up to 1.0 percent by weight of the formulation.

The antihistamines added to the topical compositions are typically from the structural classes of ethylenediamines, aminoalkylethers, and alkylamines. Among the ethylenediamine group are such antihistamines as antazoline phosphate, clemizole hydrochloride, chlorcyclizine hydrochloride, chlorothen, methapheniline hydrochloride, dorastine hydrochloride, methdilazine hydrochloride, promethazine hydrochloride, pyrathiazine hydrochloride, pyrilamine maleate, quinetolate, thenaldine, thenyldiamine hydrochloride, thonzylamine hydrochloride, tripelennamine, and zolamine hydrochloride. Among the aminoalkylether group are such antihistamines as chlorphenoxamine hydrochloride, carbinoxamine maleate, clemastine, diphenhydramine hydrochloride, diphenylpyraline hydrochloride, doxylamine succinate, and pyroxamine maleate. Among the alkamine group are such antihistamines as azatadine maleate, bromdiphenhydramine hydrochloride, cyproheptadine hydrochloride, dimethindene maleate, phenindamine tartrate, pheniramine maleate, brompheniramine maleate, dexbrompheniramine maleate, chlorpheniramine maleate, dex-chlorpheniramine maleate, closiramine, cycliramine maleate, mianserin hydrochloride, pyrrobutamine phosphate, terfenadine, and triprolidine hydrochloride. Besides the above, some compositions in structural groups, which groups are not primarily antihistamines such as phenothiazines, piperidines, and piperazines, have antihistaminic characteristics. These groups include promethazine, astemizole, fexofenadine, loratadine, desloratadine, terfenadine, cetirizine, and meclizin, which are antihistaminic.

Another active ingredient used in the formulations hereof is the employment of a topical anesthetic in conjunction with the antipruritic and demulcent effect of the acorn derivative. Here in by the addition of this class of compounds, the user experiences the reversible abolition of sensory perception, especially the sensations of pain and extreme irritation. While some of these topical anesthetic compounds are structurally related to the antihistamines in the preceding paragraph, the compounds take on a disinct role in preparations described. The first group are esters of benzoic acid and diethylaminoethyl alcohols, namely, benzocaine, chloroprocaine, procaine, and tetracaine. Other synthetic anesthetic compounds, which are not esters of benzoic acid and are pharmacologically grouped together, are bupivacaine, dibucaine, lidocaine, mepivacaine, and prilocaine. Besides these two groups, the compounds of etidocaine and pramoxine are also applicable. In one of the topical spray formulations described below the anesthetic, pramoxine hydrochloride, comprises up to 1.0 percent by weight thereof.

Colloidal oatmeal, when used in the formulations hereinbelow, because of the hydrophilic nature thereof, acts at the site of application to control the osmotic pressure of water with respect to the skin and permits adequate water to enter into the stratum corneum. Oatmeal leaves an occlusive film on the skin that serves to hold in moisture, which protects the skin against irritation and acts as an antipruritic. The USP grade of colloidal oatmeal described in this invention was obtained from Beacon CMP Corporation, 611 Springfield Road, Kenilworth, N.J. 07033.

In the following examples, the carrier can be any suitable aqueous dispersion material, cream, lotion, or ointment, which may include, for example hydrocolloids, plasdone, methyl cellulose, hydroxypropyl cellulose, lanolin, mineral oil, petroleum jelly, polyalkylene glycols such as polyethylene glycols, or mixtures thereof. The formulations may contain surfactants, antioxidants, and stabilizers such as benzoic acid, sorbic acid, parabens, butylated hydroxyanisole (BHA), butylated hydroxytoluene (BHT), vitamin E, sarcosonates, pluronic, The extracts can also be combined with astringents such as witch hazel, aluminum acetate, aluminum sulfate, zinc oxide, zinc acetate, sodium bicarbonate, and calamine. The extracts can contain antihistamine products such as diphenhydramine, citerazine, Claritin, Alegra, etc. The extract may also contain colloidal oatmeal, benzyl alcohol, and bentaquatam.

EXAMPLE 1

An aqueous roasted acorn dispersion is prepared by extracting 83 grams of prepared roasted acorns per liter of purified water by boiling for about 1-hour with some water evaporation. The extract is screened to remove large particles to bring the concentration to about 0.1 to 15%. The extract is combined with methyl paraben (1.0 g), colloidal oatmeal (1.0 g) propyl paraben (0.3 g), polysorbate 80 (10 g), and Povidon (30 g), ethyl alcohol (250 mL) and brought back to a volume of 1 liter in order to prepare an aqueous dispersion that can be sprayed.

EXAMPLE 2

An ointment contains acorn ash (log), purified water (15 g), and WHITFIELD'S ointment (75 g). The total ash portion of the material is 10% by weight. This formulation is used twice daily to treat poison ivy.

EXAMPLE 3

An oil in water emulsion lotion is prepared by combining hexane extracted which has had the hexane removed by evaporation of acorn mash (35%), lanolin (15%), Steapyrium Chloride (2%), Polysorbate 80 (1%), glycerin (25%), dimethicone (5%), cyclomethicone (5%), and purified water (12%).

An aqueous dispersion prepared from acorn mash, roast, or ash may be prepared according to the following Table I.

TABLE I

| Ingredient | Amount |
| --- | --- |
| Water | 40 to 99% |
| Acorn Extract (dry solids basis) | 0.1 to 40% |
| Colloidal Oatmeal | 0 to 40% |
| Surfactant | 0.1 to 3% |
| Emulsifying agent | 0.1 to 2% |
| Hydrocol loid | 0.1 to 5% |

An ointment prepared form acorn mash, roast, or ash may be prepared according to the following Table II.

TABLE II

| Ingredient | Amount |
| --- | --- |
| Water | 0.1 to 30% |
| Acorn Extract (dry solids basis) | 0.1 to 60% |
| Colloidal Oatmeal | 0 to 60% |
| WHITFIELDS OINTMENT | 69.9 to 99.8% |

An ointment prepared form acorn mash, roast, or ash may be prepared according to the following:

TABLE III

| Ingredient | Amount |
| --- | --- |
| Water | 0 to 25% |
| Acorn Extract (dry solids basis) | 0.1 to 70% |
| Lanolin | 0 to 30% |
| Surfactant | 0.1 to 10% |
| Emulsifying agent | 0.1 to 5% |
| Glycerin | 0 to 30% |
| Dimethicone | 0 to 15% |
| Cyclomethicone | 0 to 15% |
| Mineral Oil | 0 to 30% |
| Petrolatum | 0 to 30% |

EXAMPLE 4

Basic Spray Formulation

An aqueous roasted acorn dispersion is prepared by extracting 83 grams of prepared roasted acorns per liter of purified water by boiling for about 1-hour with some water evaporation. The extract is screened thru a number 50 USA Standard Testing Sieve to remove large particles to bring the concentration to about 0.1 to 15%. The extract is combined with methyl paraben (1.0 g), propyl paraben (0.25 g), USP Menthol (2 g), poloxamer (5 g), and, ethyl alcohol (230 mL) and brought back to a volume of 1 liter in order to prepare an aqueous dispersion that can be sprayed.

| | |
| --- | --- |
| Aqueous Roasted Acorn Extract (3–5% solids) | 76.2% |
| Ethyl Alcohol | 23.0% V/V |
| Poloxamer 338 | 0.5% |
| USP Menthol | 0.2% |
| Methyl Paraben | 0.1% |
| Propyl Paraben | 0.02% |

EXAMPLE 5

Spray With Antihistamine

An aqueous roasted acorn dispersion is prepared by extracting 83 grams of prepared roasted acorns per liter of purified water by boiling for about 1-hour with some water evaporation. The extract is screened thru a number 50 USA Standard Testing Sieve to remove large particles to bring the concentration to about 0.1 to 15%. The extract is combined with methyl paraben (1.0 g), propyl paraben (0.25 g), USP Menthol (2 g), diphenhydramine hydrochloride (20 g) poloxamer (5 g), and, ethyl alcohol (230 mL) and brought back to a volume of 1 liter in order to prepare an aqueous dispersion that can be sprayed.

| | |
| --- | --- |
| Aqueous Roasted Acorn Extract (3–5% solids) | 74.2% |
| Ethyl Alcohol | 23% V/V |
| Diphenhydramine Hydrochloride | 2% |
| Poloxamer 338 | 0.5% |
| USP Menthol | 0.2% |
| Methyl Paraben | 0.1% |
| Propyl Paraben | 0.02% |

EXAMPLE 6

Spray With Topical Anesthetics

An aqueous roasted acorn dispersion is prepared by extracting 83 grams of prepared roasted acorns per liter of purified water by boiling for about 1-hour with some water evaporation. The extract is screened through a number 50 USA Standard Testing Sieve to remove large particles to bring the concentration to about 0.1 to 15%. The extract is combined with methyl paraben (1.0 g), propyl paraben (0.25 g), USP Menthol (2 g), promoxine hydrochloride (10 g) poloxamer (5 g), and, ethyl alcohol (230 mL) and brought back to a volume of 1 liter in order to prepare an aqueous dispersion that can be sprayed.

| | |
| --- | --- |
| Aqueous Roasted Acorn Extract (3–5% solids) | 74.2% |
| Ethyl Alcohol | 23% V/V |
| Pramoxine hydrochloride | 1% |
| Poloxamer 338 | 0.5% |
| USP Menthol | 0.2% |
| Methyl Paraben | 0.1% |
| Propyl Paraben | 0.02% |

EXAMPLE 7

Spray With Topical Antipruritic

An aqueous roasted acorn dispersion is prepared by extracting 83 grams of prepared roasted acorns per liter of purified water by boiling for about 1-hour with some water evaporation. The extract is screened thru a number 50 USA Standard Testing Sieve to remove large particles to bring the concentration to about 0.1 to 15%. The extract is combined with methyl paraben (1.0 g), propyl paraben (0.25 g), USP Menthol (2 g), hydrocortisone acetate (10 g), poloxamer (5 g), and, ethyl alcohol (230 mL) and brought back to a volume of 1 liter in order to prepare an aqueous dispersion that can be sprayed.

| | |
| --- | --- |
| Aqueous Roasted Acorn Extract (3–5% solids) | 74.2% |
| Ethyl Alcohol | 23.0% V/V |
| Hydrocortisone acetate | 1% |
| Poloxamer 338 | 0.5% |
| USP Menthol | 0.2% |
| Methyl Paraben | 0.1% |
| Propyl Paraben | 0.02% |

The acorn-derivative-containing medicaments hereof are formulated for external application to the affected area of the skin. The active ingredient is the acorn derivative. With initial as well as persistent application, the acorn derivative is effective to relieve the pruritic and the histaminic reaction.

Although this invention has been described with reference to the above-recited examples thereof, it will be apparent to those skilled in the art that the principles of this invention can be embodied in other forms and formulations within the scope of the claims.

What is claimed is:

1. A topical spray formulation for reducing a urushiol-induced allergic response and the dermatitis associated therewith, said spray formulation comprising:

an aqueous roasted acorn extract and a nontoxic dermatologically acceptable dispersant material; and, said acorn extract having 1.0 to 25% percent solids by weight thereof.

2. A topical spray formulation as described in claim 1, wherein said dispersant material is ethyl alcohol comprising up to 25 percent by volume of the spray formulation.

3. A topical spray formulation as described in claim 2 wherein said dispersant material further comprises a nonionic surfactant being selected from the group consisting of poloxamer; polyoxyethylene alkyl ethers; polyoxyethylene castor oil derivatives; polyoxyethylene sorbitan fatty acid esters; polyoxyethylene stearates; and mixtures thereof.

4. A topical spray formulation as described in claim 3 wherein the nonionic surfactant is poloxamer 338 comprising up to 1.0 percent by weight of the spray formulation.

5. A topical spray formulation as described in claim 2 further comprising a benzoic-acid-derived preservative being selected from the group consisting of benzoic acid; butylparaben; ethylparaben; methylparaben; propylparaben; sodium benzoate; and, mixtures thereof.

6. A topical spray formulation as described in claim 5 wherein the benzoic-acid-derived preservative is a mixture of methylparaben comprising up to 0.1 percent by weight of the spray formulation and propylparaben comprising up to 0.025 percent by weight of the spray formulation.

7. A topical spray formulation as described in claim 5 further comprising a topical antipruritic being selected from the group consisting of phenol; camphor; menthol; hydrocortisone; hydrocortisone acetate; camphorated metacresol; phenolated sodium; and, mixtures thereof.

8. A topical spray formulation as described in claim 7 wherein the topical antipruritic is menthol comprising up to 0.2 percent by weight of the spray formulation.

9. A topical spray formulation as described in claim 7 wherein the topical antipruritic is hydrocortisone acetate comprising up to 1.0 percent by weight of the spray formulation.

10. A topical spray formulation as described in claim 7 wherein the topical antipruritic is a mixture of hydrocortisone acetate comprising up to 1.0 percent by weight of the spray formulation and menthol comprising up to 0.2 percent by weight of the spray formulation.

* * * * *